United States Patent [19]

Gleaves et al.

[11] Patent Number: 5,039,489

[45] Date of Patent: Aug. 13, 1991

[54] APPARATUS FOR CATALYST ANALYSIS

[76] Inventors: John T. Gleaves, Rt. 1, Box 171 A2, Foley, Mo. 63347; Patrick T. Harkins, 2315 Callender Ct., Chesterfield, Mo. 63017

[21] Appl. No.: 513,288

[22] Filed: Apr. 17, 1990

[51] Int. Cl.[5] ............... G01N 31/10; G01N 31/12; G01N 21/72

[52] U.S. Cl. .................. 422/68.1; 422/78; 422/80; 422/50; 436/37; 436/155; 436/159

[58] Field of Search ............ 422/68.1, 78, 80, 89, 422/50, 83; 436/37, 148, 155, 159, 181, 161, 173, 52

[56] References Cited

U.S. PATENT DOCUMENTS

| 3,223,492 | 12/1965 | Geitz | 422/50 |
| 4,626,412 | 12/1986 | Ebner et al. | 422/50 |
| 4,677,244 | 6/1987 | Hachmuth et al. | 436/148 |

FOREIGN PATENT DOCUMENTS 0703704  2/1954  United Kingdom ............ 422/68.1

OTHER PUBLICATIONS

Machiels, *Development of a Pulse Reactor with On-Line MS Analysis to Study the Oxidation of Methane*, American Chemical Society, 1982.

Primary Examiner—Robert J. Warden
Assistant Examiner—Theresa A. Trembley
Attorney, Agent, or Firm—Webb, Burden, Ziesenheim & Webb

[57] ABSTRACT

An improvement in an apparatus for carrying out chemical reactions is disclosed. The apparatus includes a housing defining a vacuum chamber, with a reactor located within the vacuum chamber. The improvement comprises a device disposed within the housing having a high-pressure outlet tube for engagement with the reactor, a bypass for placing the high-pressure outlet tube in fluid communication with the outside of the vacuum chamber, an orifice for placing the high-pressure outlet tube in fluid communication with the vacuum chamber and at least one valve for selectively opening or closing the bypass and the orifice. The device may be engaged and disengaged with the reactor by a manual shaft and gear arrangement for operating the reactor at higher pressures relative to the normal vacuum operation.

27 Claims, 5 Drawing Sheets

A – MASS 44 AFTER 3 REDUCTION CYCLES
B – MASS 44 AFTER 5 REDUCTION CYCLES

Fig. 6

A – MASS 44 – CARBON DIOXIDE
B – MASS 48 – ETHYLENE OXIDE

Fig. 7

APPARATUS FOR CATALYST ANALYSIS

BACKGROUND OF THE INVENTION

1. Field of the Invention

This invention relates to apparatuses for carrying out catalyzed chemical reactions, and more particularly to apparatuses for studying catalysts by real-time analysis of reaction products.

2. Description of the Prior Art

Basic information about the physical and chemical processes involved in catalytic reactions, such as reaction intermediates, reaction mechanisms, absorption and desorption of reactants and products in catalytic reactions, oxidation and reduction of catalysts, catalyst poisons, the concentration of reactants on a catalyst surface, etc., has heretofore been obtained using techniques such as molecular beam mass spectrometry, modulated molecular beam mass spectrometry, thermal desorption experiments, and temporal analysis of products ("TAP"). TAP is generally a technique for real-time analysis of reaction products, i.e., detection and analysis are carried out as nearly as possible to the instant of reaction, before further reaction of the products or further reaction of fragile and reactive intermediates. See, for example, U.S. Pat. No. 4,626,412 to Ebner et al.

The nature of certain techniques for analysis of catalytic reactions dictates that they be carried out in a vacuum. The vacuum is necessary to achieve molecular flow through the reactor as well as to operate the mass spectrometer, a common instrument utilized in analyzing reaction products and intermediates. However, the necessity of creating a vacuum has greatly limited the conditions which a researcher can impose on his experiment. For example, it has been found desirable to conduct certain catalytic reaction experiments at conditions of standard temperature and pressure. Current vacuum systems for real-time analysis are incapable of creating such conditions, and thus their usage has been unduly limited.

SUMMARY OF THE INVENTION

Accordingly, we have invented an improvement in an apparatus for carrying out catalyzed chemical reactions which permits the operator to rapidly switch from one set of experimental conditions to another and to examine a variety of pressure regimes using the same catalyst sample. The apparatus includes a housing defining a vacuum chamber and means for producing a vacuum therein. A reactor is located within the vacuum chamber, the reactor allowing for passage of a reactant gas or gas mixture into the reactor and a product gas out of the reactor. The improvement comprises a device which is disposed within the housing for operating the reactor at higher pressures relative to the normal vacuum operation.

The device includes a high-pressure outlet tube for engagement with the reactor to receive the product gas, means for providing a pressure-tight seal between the reactor and the high-pressure outlet tube, and a bypass for placing the high-pressure outlet tube in fluid communication with the outside of the housing. The device also includes an orifice for placing the high-pressure outlet tube in fluid communication with the vacuum chamber and at least one valve for selectively opening or closing the bypass and the orifice. Means are also included for maintaining elevated pressures within the device and the reactor when the high-pressure outlet tube and the reactor are engaged, as well as means for selectively engaging or disengaging the device from the reactor.

The means for providing a pressure-tight seal between the reactor and the high-pressure outlet tube may include an O-ring interposed between the high-pressure outlet tube and the reactor. The O-ring may further be mounted on a sealing flange, which itself may be in direct contact with a spring that exerts a compressive force on the sealing flange, placing the O-ring in pressure-tight contact with the reactor. Means for extending or retracting the spring may also be provided.

The device may further include means for cooling the sealing flange when the high-pressure outlet tube is engaged on the reactor, and the at least one valve may be a solenoid valve or an air actuated valve. The orifice may receive a capillary tube, and the means for maintaining pressure within the device may include a back-pressure regulator in fluid communication with the bypass. When the capillary tube is utilized, the at least one valve may include a rotary seat valve disposed upstream of the capillary tube for opening and closing the capillary tube.

The means for selectively engaging or disengaging the device from the reactor may include a linear slide which is integral with the device and which may be displaced by a drive assembly, with the drive assembly preferably being threadingly connected to a journaled drive shaft whereby rotation or counter-rotation of the drive shaft will vertically displace the linear slide. The drive assembly may further include a knob affixed to the drive shaft for manual rotation of the drive shaft.

A mass spectrometer may be disposed inside of the housing, and a gas chromatograph may be disposed outside of the housing.

Further features and advantages of the present invention will become apparent from the following more detailed description in conjunction with the accompanying drawings.

DETAILED DESCRIPTION OF THE PREFERRED EMBODIMENTS

Our invention is a device which may be incorporated in an apparatus for carrying out and analyzing chemical reactions for providing capability in the apparatus to conduct experiments at pressures of 0.0001 to 1 atmosphere or greater. The invention is particularly suitable for attachment to temporal analysis of products systems ("TAPS"), which normally may be operated only at vacuum pressures. A method and apparatus for carrying out catalyzed chemical reactions and for studying catalysts with TAPS systems is disclosed more fully in U.S. Pat. No. 4,626,412 to Ebner et al., incorporated herein by reference.

Figure 1:
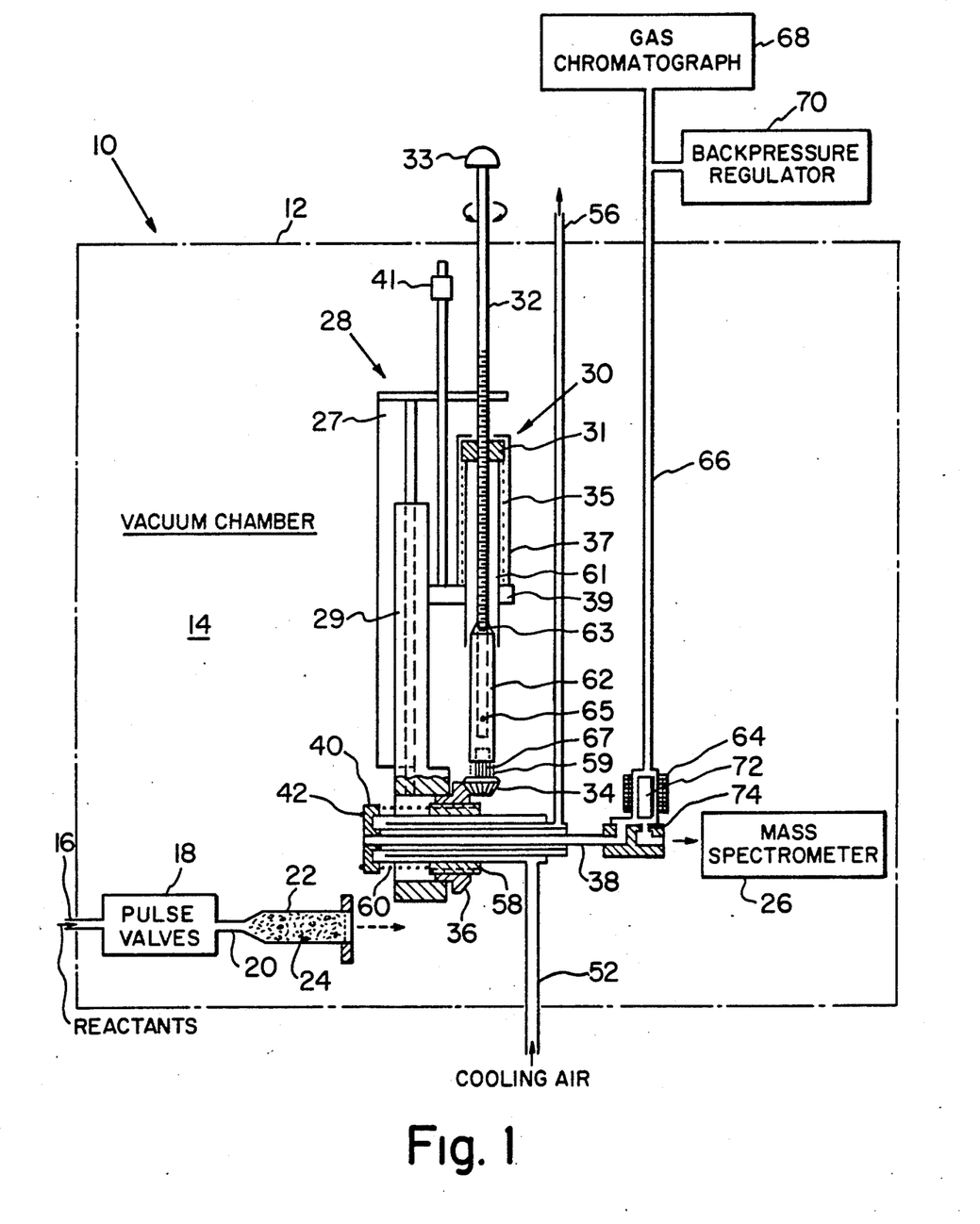
FIG. 1 is schematic view of an apparatus for carrying out and analyzing chemical reactions with the improvement of the present invention in the disengaged position.

FIG. 1 is a schematic depiction of a TAPS system 10 utilizing the improvement of the present invention. The TAPS system 10 includes a housing 12 defining a sealed vacuum chamber 14 in which the bulk of the components of the system are located. A vacuum may be achieved in the vacuum chamber by means of a vacuum pump, including but not limited to oil diffusion pumps, turbo molecular pumps, ion pumps, and cryopumps (not shown).

Reactants are fed into the system via inlet 16, and they then pass through a series of pulse or continuous flow valves 18 where they may be selectively fed through pulse valve inlet 20 to a reactor 22. A plurality of catalyst particles 24 are disposed within the reactor 22, and these may be of varying composition depending on the type of reaction desired to be carried out.

Under normal vacuum operating conditions, the reaction products and intermediates would be drawn out of the reactor 22 and into the vacuum chamber 14. A mass spectrometer 26 is commonly disposed in fluid communication with the vacuum chamber 14, thereby providing temporal analysis of the reaction products and intermediates. FIG. 1 shows a device 28 in accordance with the present invention for operating the reactor 22 at higher pressures relative to the normal vacuum operation. The device 28 is also shown within the housing 12 in a first position disengaged from the reactor 22.

Figure 2:
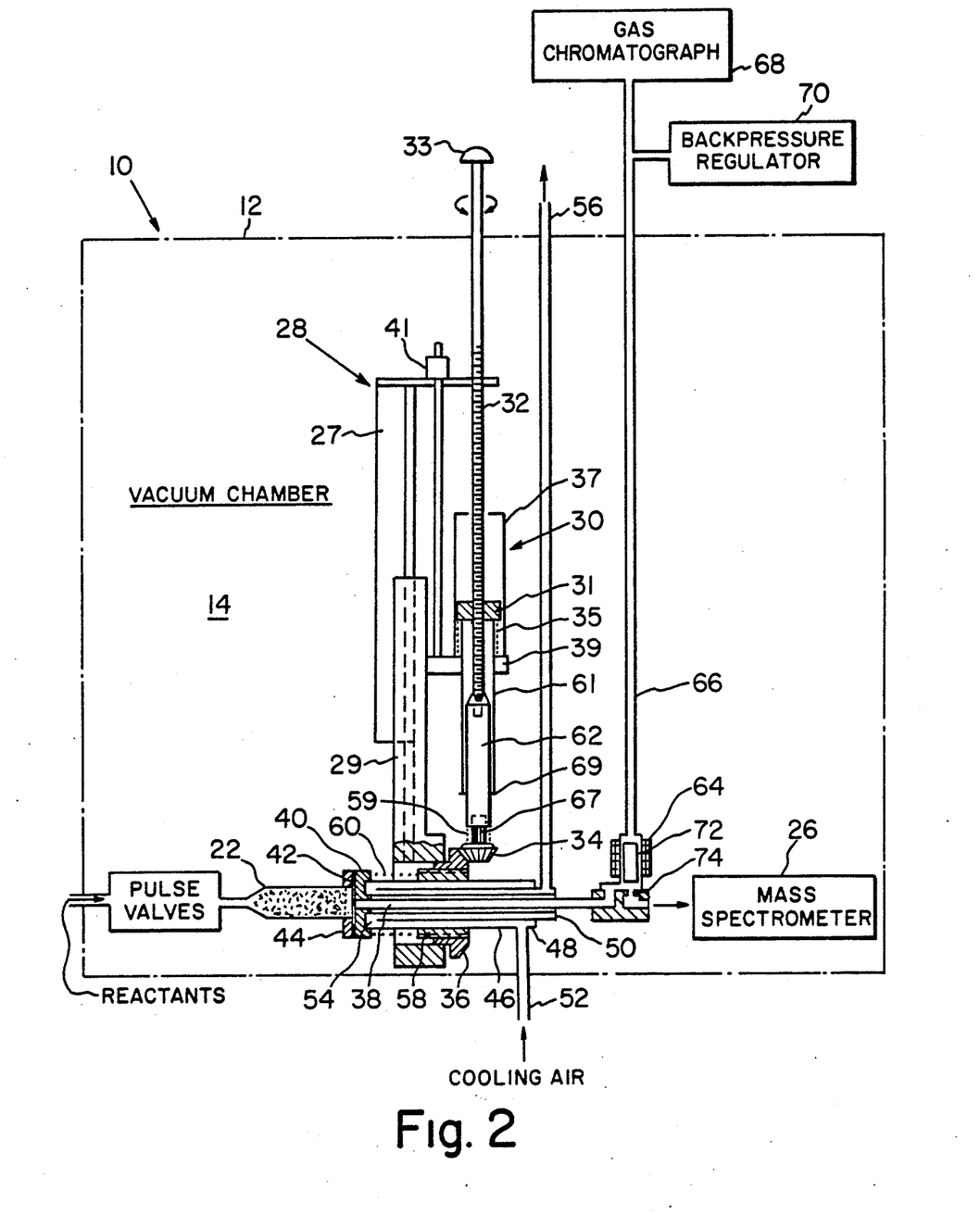
FIG. 2 is a schematic view of the apparatus of FIG. 1 with the improvement of the present invention in the engaged position.

Referring now to FIG. 2, the device 28 is shown in a second position engaged on the reactor 22 for receiving reaction products and intermediates. The device 28 may be selectively engaged or disengaged from the reactor 22 by means of a linear slide 29 which is integral with the device 28 and which is mounted on a fixed support 27. A drive assembly 30 is in mechanical communication with the linear slide 29, and the drive assembly threadingly receives a journaled drive shaft 32 which, when rotated by a knob 33, causes vertical displacement of the linear slide 29. Specifically, a traveling nut 31 engages a spring 35 and is fixed against rotation by a bearing cover 37. As the drive shaft 32 rotates, the traveling nut moves downward, pressing against the spring 35 which itself rests on a plate 39. The plate 39 is fixed to the linear slide 29, and thus, as it is forced downward, so is the linear slide. A stop 41 assures that the linear slide 29 will not travel further than required to place the device 28 in proper alignment with the reactor 22.

The drive shaft 32 has a horizontal gear 34 disposed adjacent to its lower end. The horizontal gear 34 is engaged to a corresponding vertical gear 36 for translating motion from the drive shaft 32 to a portion of the device 28 which will be discussed in further detail below. While the presently preferred embodiment displaces the device 28 by manual shaft and gear means, it will be understood that displacement could equally be achieved by electric or air driven configurations.

When the device 28 is engaged on the reactor 22, a high-pressure outlet tube 38 is placed in fluid communication with the reactor 22 for receiving product gas. More specifically, a sealing flange 40 is positioned adjacent the inlet of the high-pressure outlet tube 38. An O-ring 42 is mounted to the sealing flange 40. When the device 28 is engaged on the reactor 22, the sealing flange 40 and the O-ring 42 are urged into compressive contact with a flange 44 adjacent the outlet of the reactor 22. Thus, a pressure-tight seal between the reactor 22 and the high-pressure outlet tube 38 is formed.

Due to high temperatures incurred in operation of the reactor 22 for carrying out chemical reactions, the sealing flange 40 and the O-ring 42 are air cooled by means of a cooling sleeve 46 which is exterior to and concentric with the high-pressure outlet tube 38. Preferably, the cooling sleeve is designed to prevent decomposition of the O-ring 42 and the sealing flange 40 at elevated temperatures exceeding 500° C.

The cooling sleeve 46 more particularly comprises an outer layer 48 and an inner layer 50, cooling air being first introduced to the outer layer through an inlet 52 and circulated by means of a vent 54 to the inner layer 50, ultimately being expelled through an outlet 56. Ambient air under pressure is introduced into the cooling sleeve 46 through inlet 52 from a cylinder or the like located outside the housing 12. The air is simply expelled to ambient through the outlet 56, avoiding any leakage into the vacuum chamber 14 which would contaminate the experiment.

Encircling the cooling sleeve 46 is a threaded tube 58 which is affixed to the vertical gear 36 and which has a spring 60 extending therefrom. The spring 60 makes contact with the sealing flange 40, thus biasing the O-ring 42 against the flange 44 of the reactor 22. The vertical gear 36 is rotatably mounted on the cooling sleeve 46 while the threaded tube 58 is mounted in such a way as to prevent rotation relative to the vertical gear 36. Thus, rotation of the drive shaft 32 and the appending horizontal gear 34 in a first direction will cause extension of the sealing flange 40 in the direction of the reactor 22, while counter-rotation of the drive shaft will cause retraction of the sealing flange 40.

More specifically, a first sleeve 61 and a second sleeve 62 are telescopically mounted to the drive shaft 32 as shown in FIG. 1. The second sleeve is of lesser diameter than the first sleeve, and the second sleeve has an angled slot 63 at its upper end. The horizontal gear 34 is mounted to the second sleeve 62 by a spline 67 with a spring 59 interposed between the second sleeve and the horizontal gear. The first sleeve 61 is affixed to the traveling nut 31. After the stop 41 is engaged on the fixed support 27, the traveling nut 31 compresses the first sleeve 61 until it engages a flange 69 located on the second sleeve 62. The second sleeve is then forced downward until the slot 63 is aligned with a pin 65 on the drive shaft 32. Here, the edges of the slot 63 engage the pin 65, which is affixed to the drive shaft, and rotation of the drive shaft 32 now causes rotation of the second sleeve 62. The second sleeve engages the spline 67 affixed to the horizontal gear 34, thereby rotating the horizontal gear and ultimately urging the threaded tube 58 against the spring 60. The spring 60 compresses the sealing flange 40 and the O-ring 42 against the flange 44 on the reactor 22.

Positioned at the downstream end of the high-pressure outlet tube 38 is a valve assembly 64 for placing the high-pressure outlet tube 38 in fluid communication with a bypass 66. The bypass 66 is in fluid communication with the outside of the housing 12, feeding reaction products to an analytical machine or machines such as a gas chromatograph 68. The bypass 66 is also in fluid communication with a backpressure regulator 70 which maintains elevated pressures within the device 28 and the reactor 22 when the high-pressure outlet tube 38 and the reactor 22 are engaged.

Fluid communication between the high-pressure outlet tube 38 and the bypass 66 is controlled by a first valve 72 which may either be of the solenoid or air driven type such as those well known in the art. An orifice 74 is also included on the valve assembly 64 for placing the high-pressure outlet tube 38 in fluid communication with the vacuum chamber 14. The first valve 72 may serve the dual function of controlling fluid communication between the high-pressure outlet tube 38 and the orifice 74 when bypassing the reaction products to the outside of the housing 12. The first valve 72 is simply rested on top of the orifice 74, and this placement of the valve upstream of the orifice 74 provides the added advantage of preventing clogging or plugging of the orifice 74 when fluid communication of the high-pressure outlet tube 38 with the vacuum chamber 14 is not desired.

Figure 3:
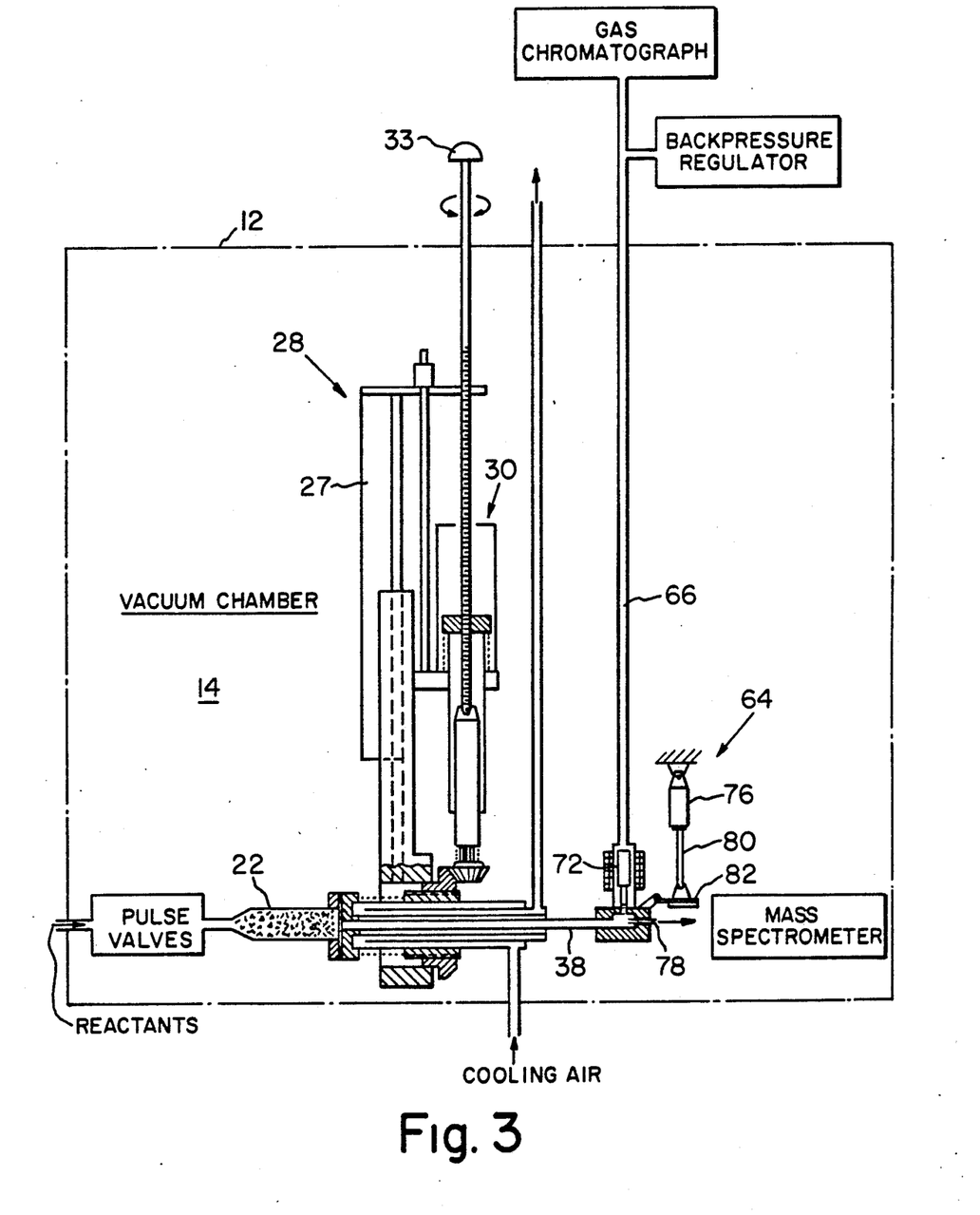
FIG. 3 is a schematic view of the apparatus of FIG. 1 with a second embodiment of the improvement in the engaged position.
Figure 4:
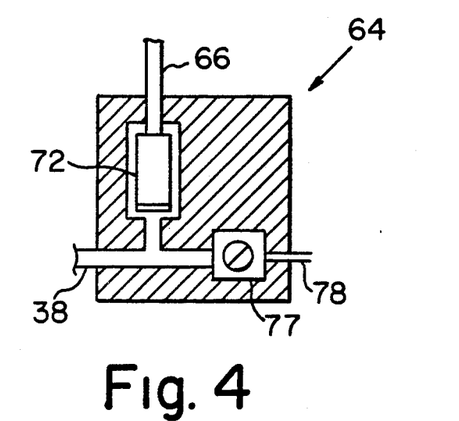
FIG. 4 is a schematic view of a third embodiment of the improvement in accordance with the present invention.

Referring to FIG. 3, a second preferred embodiment of the valve assembly 64 is shown having a second valve 76 distinctly responsible for controlling fluid communication between the high-pressure outlet tube 38 and the vacuum chamber 14. A further feature of the second preferred embodiment is placement of a replaceable capillary tube 78 in the orifice 74, which provides flexibility in choosing orifice diameter and which generally provides the capability of utilizing a leak to the vacuum chamber 14 which is of much smaller diameter than the orifice 74. As shown in FIG. 3, the second valve is of the solenoid type having a piston 80 which is in direct contract with a retractable shutter 82 which, when the piston 80 is extended, is forced over the outlet of the capillary tube 78. It will appreciated by those skilled in the art that the second valve may alternatively be placed upstream of the capillary tube 78 with the added advantages relating to clogging discussed above. Additionally, the second valve may include a rotating seat valve 77, such as that shown in FIG. 4, or it could be a ball valve, either of which are well known in the art.

When the device 28 is incorporated into a conventional TAP system, the operator is able to select a much wider range of experimental conditions to which the reactants will be exposed, and thus increased understanding of catalysts and development of catalytic processes is fostered. When the device 28 is engaged on the reactor 22, the operator can, through manipulation of the valve(s), direct flow of product gases either to the gas chromatograph through the first valve 72 and the bypass 66 or to the mass spectrometer through the orifice 74. Use of the replaceable capillary tube 78 in the orifice 74 can provide a leak to the vacuum chamber 14 of varying diameter, thus permitting the operator to easily change the flow rate of product gases to the mass spectrometer.

The device 28 may be disengaged from the reactor 22 and moved out of position while the vacuum chamber 14 is under a vacuum. This permits the operator to rapidly switch from one set of experimental conditions to another and to examine a variety of pressure regimes using the same catalyst sample. It will be apparent to those skilled in the art that the valve assembly 64 and the bypass 66 may be equipped with a heating element to control temperature and prevent undesirable condensation of high temperature product gases.

Employment of the device 28 in conventional TAP systems provides for obtainment of both mass spectrometry and gas chromatography data during a single run of a given catalyst sample. Such capability is not present in conventional TAP systems. With the improvement of the present invention, the sample can be cycled between high and low pressure conditions simply by engaging and disengaging the device 28, and new information can be obtained which would not be obtainable from TAP low-pressure experiments alone.

To demonstrate the capabilities of the TAP system equipped with the improvement of the present invention, a series of experiments were performed using the selective oxidation of ethylene over silver metal as a test reaction. In all experiments, the reactor 22 was initially loaded with a 0.5 gram sample of 300 micron silver power obtained from a commercial source and used without further pretreatment. Reaction studies were performed by flowing or pulsing a single gas or gas mixture through the reactor 22 with the device 28 engaged or disengaged. The reactant gases used in these studies contained typically one or more of the following components: oxygen-16, ethylene, and ethylene-d4.

EXAMPLE I

A silver sample was placed in the reactor 22 and the device 28 was engaged. The vacuum chamber 14 was then evacuated to $10^{-6}$ torr while the reactor 22 was held at a pressure of 800 torr by introducing a flow of oxygen into the reactor 22 via the inlet 16. Gas flowing through the reactor 22 exited by means of the capillary tube 78 mounted in the orifice 74 of the valve assembly 64, flowing into the vacuum chamber 14. Under these conditions, the pressure in the vacuum chamber was typically $1 \times 10^{-4}$ to $5 \times 10^{-5}$ torr. It was determined that the pressure in the reactor 22 could be easily varied from a few torr to 1500 torr by adjusting the pressure of the oxygen feed in coordination with the backpressure regulator 70.

Similar experiments were performed at various pressures with different mixtures of oxygen and ethylene. In these experiments, the product gases were analyzed by allowing the product gases to flow to the mass spectrometer via the capillary tube 78. In another set of experiments, a portion of the product gas was diverted to the gas chromatograph and the product gas was analyzed using both the mass spectrometer and the gas chromatograph. It was determined that either device could be employed to determine the various components in a gas mixture, and complementary data could be obtained by taking mass spectrometry data at the instant the gas chromatograph sample was obtained.

Figure 5:
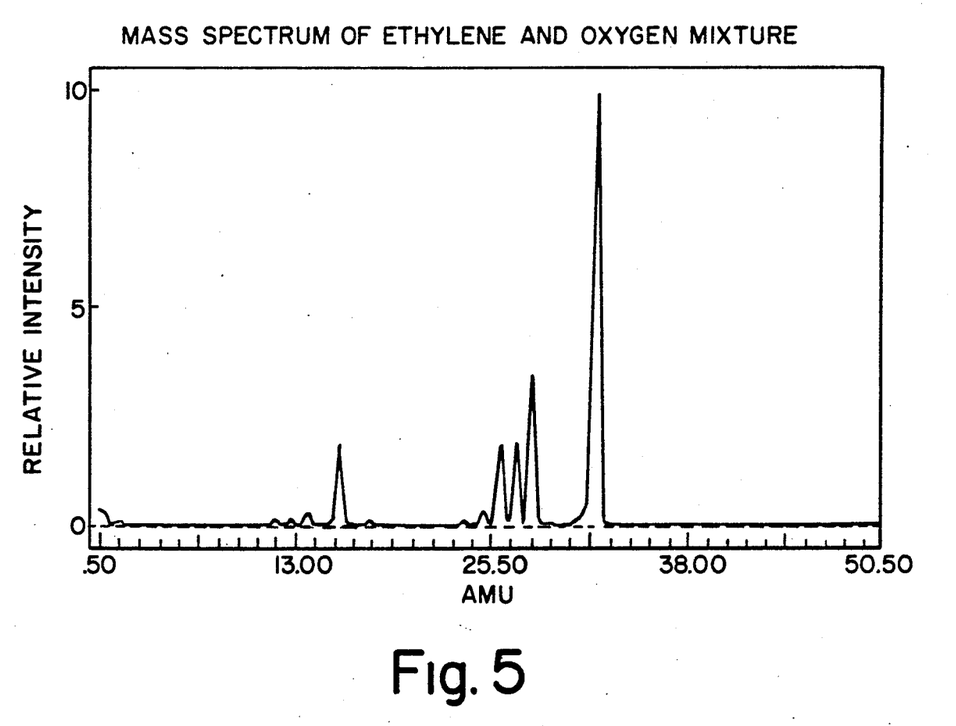
FIG. 5 is a graphical representation of the mass spectrum of an ethylene and oxygen mixture.

In addition, it was determined that the gas composition of the mixture could be easily maintained at a relatively constant value (varying less than 2%) over an extended period of time (i.e., eight hours). A typical mass spectrum of a gas mixture flowing through the reactor 22 and exiting the capillary tube 78 is shown in FIG. 5.

These experiments demonstrated that the TAP reactor 22, when equipped with the improvement of the present invention, may be maintained at pressures significantly above those encountered in a typical TAP experiment, and that high pressure continuous flow experiments could be performed, and finally that data could be collected in a complementary fashion with either a gas chromatograph or a mass spectrometer detector.

EXAMPLE II

A silver sample was placed in the reactor 22 and the device 28 engaged thereon. The vacuum chamber 14 was then evacuated to $10^{-6}$ torr while the pressure in the reactor 22 was held at 800 torr by introducing a flow of oxygen into the reactor 22 via inlet 16. The reactor 22 was then heated to 100°, 200°, 300°, and 400° C. to determine if a gas-tight seal could be maintained between the reactor 22 and the high-pressure outlet tube 38 at elevated temperatures. Gas flowing through the reactor 22 exited by means of the capillary tube 78 and flowed into the vacuum chamber 14. The pressure in the vacuum chamber 14 was monitored with an ionization gauge and over the course of the heating, it was found that the ionization gauge gave a constant signal corresponding to a pressure of $2.2 \times 10^{-4}$ torr. This demonstrated that a gas-tight seal was in fact maintained. A similar experiment was performed in which the capillary tube 78 was closed by the second valve 76. In this case, the pressure in the vacuum chamber 14 never rose above $10^{-6}$ torr. This further demonstrated the effectiveness of the gas-tight seal at elevated temperatures.

EXAMPLE III

A silver sample was placed in the reactor 22 and the device 28 was engaged. The vacuum chamber 14 was then evacuated to $10^{-6}$ torr while the pressure in the reactor 22 was held at 760 torr by introducing a 19.0 cc/min. (STP) flow of oxygen into the reactor 22 via inlet 16. The reactor was then heated to 250° C. and the reactor product gas, exiting by means of capillary tube 78, was analyzed with the mass spectrometer. The reactor pressure and temperature were held constant for 30 minutes under a constant oxygen flow after which the feed gas was switched from oxygen to an oxygen-ethylene blend containing 12.3% $C_2H_4$ and 80.7% $O_2$. During the switch, the reactor temperature and pressure remained constant.

The composition of the product gas from the reactor 22 was continuously monitored with the mass spectrometer and a switch from the oxygen feed to the oxygen-ethylene blend was readily observable. After the composition of the product gas had stabilized, its mass spectrum was collected and stored in computer memory. It was found to consist primarily of peaks due to the parent and fragmentation ions of oxygen and ethylene.

Figure 6:
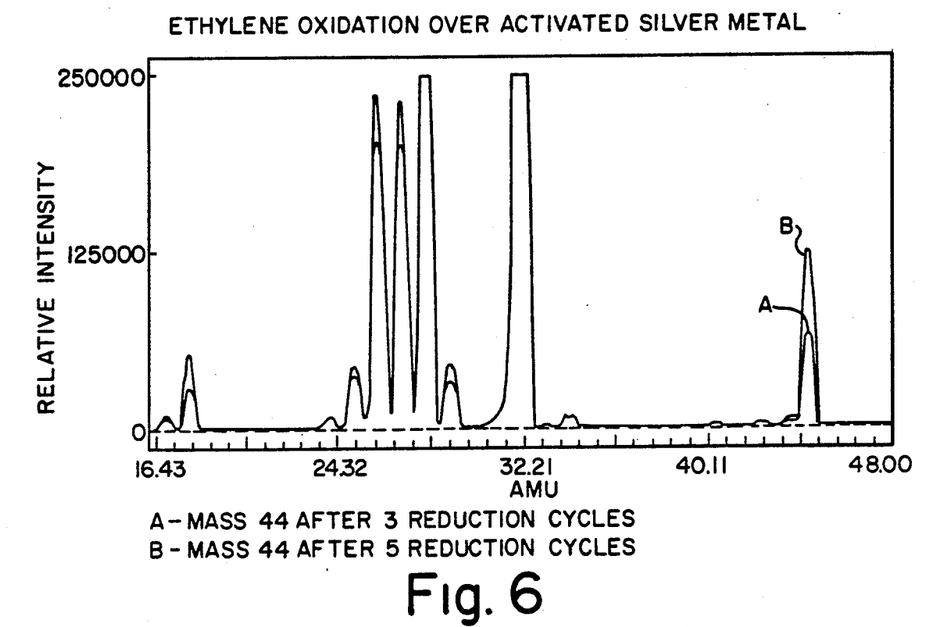
FIG. 6 is a graphical representation of ethylene oxidation over activated silver metal.

Next, the reactor feed was switched to ethylene and the reactor temperature raised to 350° C. The reactor was held at these conditions for 30 minutes and then cooled to 250° C. At this time, the feed was again switched to the oxygen-ethylene blend, and a mass spectrum was collected. The feed was then cycled between ethylene and oxygen-ethylene blends several more times until the mass spectrum of the oxygen-ethylene blend gave a constant product distribution. FIG. 6 shows the mass spectrum obtained after three and five reduction cycles. Mass peaks labeled A and B cannot be attributed to ethylene or oxygen but must correspond to a new product with a molecular weight of 44. This new product peak can be attributed to either ethylene oxide, carbon dioxide or a mixture of the two. Mass peak A was collected after three reduction cycles and mass peak B was collected after five reduction cycles.

The increased intensity of the mass 44 peak indicates that the reduction cycles increased the amount of reaction product formed. This improvement in catalyst activity has been observed by other researchers using other types of reactor systems. This demonstrates that with the present invention engaged, a catalyst sample may be activated at conventional reaction conditions, and catalytic reactions can be investigated at elevated temperatures and pressures. Our reaction data is consistent with other microreactor experiments run under similar conditions, such microreactors not having the vacuum-high pressure dual capability of the present invention.

EXAMPLE IV

After the silver sample was activated by the procedure described in Example III, the device 28 was disengaged and the continuous feed of oxygen and ethylene was shut off. A series of pulsed experiments were then performed with the reactor operated at the vacuum conditions normally encountered in a TAP type experiment. TAP transient data was collected in the pump-probe format by adjusting the mass spectrometer to a specific mass peak and tracking its intensity and time. After 100 pulses of data were collected and signals averaged, a second mass peak corresponding to a different product was collected in a similar fashion. Data collection continued until all desired product peaks were analyzed.

Figure 7:
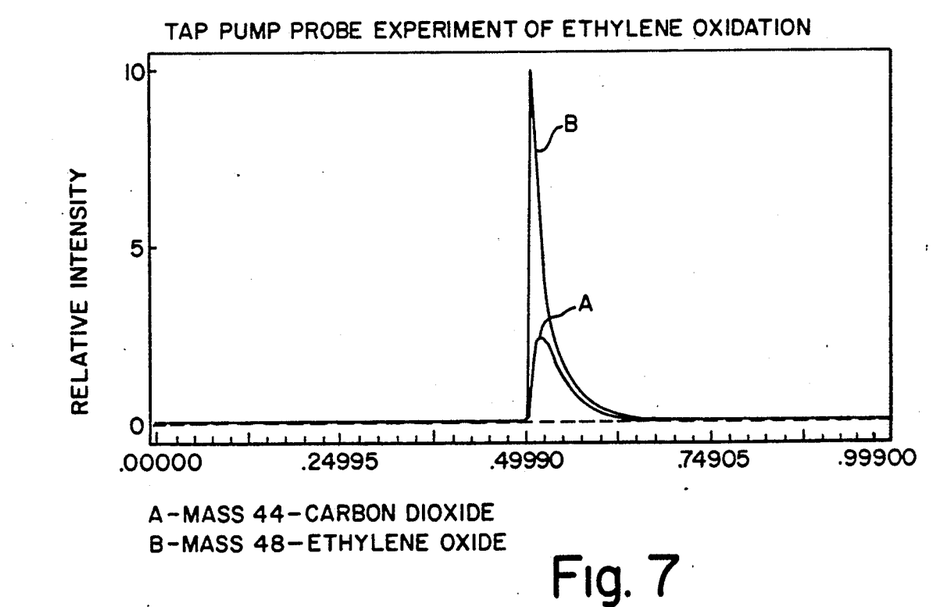
FIG. 7 is a graphical representation of a TAP pump probe experiment of ethylene oxidation.

FIG. 7 shows the pulsed data for mass peaks 44 (curve A) and 48 (curve B) corresponding to products carbon dioxide and ethylene oxide-d4. These data indicate that the silver previously activated by the procedure in Example III was active under conventional TAP experimental conditions and produced transient spectra similar to that from other TAP experiments.

An additional set of experiments were performed with a silver sample which had not been activated by the procedure in Example III. A sample was placed in the reactor 22 and the vacuum chamber 14 was pumped down without the device 28 engaged. The sample was then cycled through a series of low pressure oxidation-reduction cycles similar to those performed with the device 28 engaged. In this case, however, the absolute pressure in the reactor 22 was significantly lower. The reactor was then heated to 250° C. and ethylene-d4 and oxygen were pulsed over the catalyst as before. An examination of the mass spectrum revealed that no ethylene oxide-d4 or carbon dioxide was produced. These results indicate that the pretreatment of a catalyst using the improvement of the present invention can produce a significantly different catalyst from that obtained by pretreatment at the lower pressures of conventional TAP experiments.

Having described the presently preferred embodiments of the invention, it will be understood that the foregoing description is not intended to limit the invention except within the scope of the following claims.

We claim:

1. In an apparatus for carrying out and analyzing chemical reactions, said apparatus having a housing defining a vacuum chamber and means for producing a vacuum therein, a reactor located within the vacuum chamber, said reactor allowing for passage of a reactant gas or gas mixture into the reactor and a product gas out of the reactor, the improvement comprising a device disposed within said housing for operating the reactor at higher pressures relative to the normal vacuum operation, said device including:

a high-pressure outlet tube for engagement with the reactor to receive the product gas;

means for providing a pressure-tight seal between the reactor and the high-pressure outlet tube;

a bypass for placing the high-pressure outlet tube in fluid communication with the outside of the vacuum chamber;

an orifice for placing the high-pressure outlet tube in fluid communication with the vacuum chamber;

at least one valve for selectively opening or closing the bypass and the orifice;

means for maintaining elevated pressures relative to normal vacuum pressures within the device and the reactor when the high-pressure outlet tube and the reactor are engaged; and means for selectively engaging or disengaging the device from the reactor.

2. The device of claim 1 wherein said means for providing a pressure-tight seal between the reactor and the high-pressure outlet tube includes an O-ring interposed between the high-pressure outlet tube and the reactor.

3. The device of claim 2 further including a sealing flange on the high-pressure outlet tube, said O-ring mounted on the sealing flange.

4. The device of claim 3 further including a spring which exerts a compressive force on the sealing flange, placing the O-ring in pressure-tight contact with the reactor.

5. The device of claim 4 further including means for extending or retracting said spring.

6. The device of claim 3 further including means for cooling the sealing flange when the high pressure outlet tube is engaged on the reactor.

7. The device of claim 1 wherein said at least one valve includes a solenoid valve.

8. The device of claim 1 wherein said at least one valve includes an air actuated valve.

9. The device of claim 1 wherein said orifice receives a capillary tube.

10. The device of claim 9 wherein said at least one valve includes a rotating seat valve disposed adjacent to and in fluid communication with an inlet of the capillary tube for opening and closing the capillary tube.

11. The device of claim 9 wherein said at least one valve includes a shutter hingedly connected adjacent to and in fluid communication with an outlet of the capillary tube for opening and closing the capillary tube.

12. The device of claim 1 wherein said means for maintaining pressure within said device includes a backpressure regulator in fluid communication with said bypass.

13. The device of claim 1 wherein said means for selectively engaging or disengaging the device from the reactor includes a linear slide which is integral with the device and which may be displaced by a drive assembly.

14. The device of claim 13 wherein said drive assembly includes a journaled drive shaft which is threadingly connected to a traveling nut whereby rotation or counter-rotation of the drive shaft vertically displaces the traveling nut whose movement is translated to the linear slide by a plate fixed to the linear slide and a spring interposed between the traveling nut and the plate.

15. The device of claim 14 wherein said drive assembly further includes a knob affixed to the drive shaft for manual rotation of the drive shaft.

16. In an apparatus for carrying out catalyzed chemical reactions and studying catalysts, said apparatus having a housing defining a vacuum chamber and means for producing a vacuum therein, a reactor located within the vacuum chamber, said reactor allowing for passage of a reactant gas or gas mixture into the reactor and a product gas out of the reactor, a mass spectrometer inside the vacuum chamber and a gas chromatograph outside the vacuum chamber, the improvement comprising a device disposed within said housing for operating the reactor at higher pressures relative to the normal vacuum operation, said device including:

a high-pressure outlet tube for engagement with the reactor to receive the product gas;

a sealing flange disposed adjacent the inlet of the high-pressure outlet tube;

an O-ring interposed between the reactor and the high-pressure outlet tube and mounted on the sealing flange for providing a pressure-tight seal;

a bypass for placing the high-pressure outlet tube in fluid communication with the gas chromatograph;

an orifice for placing the high-pressure outlet tube in fluid communication with the mass spectrometer;

at least one valve for selectively opening or closing the bypass and the orifice;

a backpressure regulator in fluid communication with the bypass to maintain elevated pressures relative to normal vacuum pressures within the device and the reactor when the high-pressure outlet tube is engaged on the reactor; and means for displacing the device for engagement and disengagement of the high-pressure outlet tube and the reactor.

17. The device of claim 16 further including a spring on the high-pressure outlet tube which exerts a compressive force on the sealing flange, placing the O-ring in pressure-tight contact with the reactor.

18. The device of claim 17 further including means for extending or retracting said spring.

19. The device of claim 16 further including means for cooling the sealing flange when the high-pressure outlet tube is engaged on the reactor.

20. The device of claim 16 wherein said at least one valve includes a solenoid valve.

21. The device of claim 16 wherein said at least one valve includes an air actuated valve.

22. The device of claim 16 wherein said orifice receives a capillary tube.

23. The device of claim 22 wherein said at least one valve includes a rotating seat valve disposed adjacent to and in fluid communication with an inlet of the capillary tube for opening and closing the capillary tube.

24. The device of claim 22 wherein said at least one valve includes a shutter hingedly connected adjacent to and in fluid communication with an outlet of the capillary tube for opening and closing the capillary tube.

25. The device of claim 16 wherein said means for displacing the device includes a linear slide which is integral with the device and which may be displaced by a drive assembly.

26. The device of claim 25 wherein said drive assembly includes a journaled drive shaft which is threadingly connected to a traveling nut whereby rotation or counter-rotation of the drive shaft vertically displaces the traveling nut whose movement is translated to the linear slide by a plate fixed to the linear slide and a spring interposed between the traveling nut and the plate.

27. The device of claim 26 wherein said drive assembly further includes a knob affixed to the drive shaft for manual rotation of the drive shaft.

* * * * *